(12) United States Patent
Durousseau

(10) Patent No.: US 6,708,051 B1
(45) Date of Patent: Mar. 16, 2004

(54) FMRI COMPATIBLE ELECTRODE AND ELECTRODE PLACEMENT TECHNIQUES

(75) Inventor: Donald R. Durousseau, Purcellville, VA (US)

(73) Assignee: Compumedics Limited (AU)

( * ) Notice: Subject to any disclaimer, the term of this patent is extended or adjusted under 35 U.S.C. 154(b) by 0 days.

(21) Appl. No.: 09/831,687
(22) PCT Filed: Nov. 10, 1999
(86) PCT No.: PCT/US99/26459
§ 371 (c)(1),
(2), (4) Date: Aug. 29, 2001
(87) PCT Pub. No.: WO00/27279
PCT Pub. Date: May 18, 2000

Related U.S. Application Data
(60) Provisional application No. 60/107,918, filed on Nov. 10, 1998.

(51) Int. Cl.[7] .................................................. A61B 5/04
(52) U.S. Cl. ...................... 600/383; 600/395; 600/410
(58) Field of Search ................................. 600/372, 382, 600/383, 393, 395, 410, 411, 421

(56) References Cited

U.S. PATENT DOCUMENTS

| | | | | |
|---|---|---|---|---|
| 4,989,608 A | * | 2/1991 | Ratner | 128/653 |
| 5,044,368 A | | 9/1991 | Putz | 600/377 |
| 5,217,010 A | | 6/1993 | Tsitlik et al. | 607/9 |
| 5,291,888 A | * | 3/1994 | Tucker | 600/383 |
| 5,411,545 A | | 5/1995 | Breyen et al. | 607/122 |
| 6,073,039 A | * | 6/2000 | Berson | 600/372 |
| 6,272,370 B1 | * | 8/2001 | Gillies et al. | 600/411 |

* cited by examiner

Primary Examiner—Carl Layno
(74) Attorney, Agent, or Firm—Fulbright & Jaworski, L.L.P.

(57) ABSTRACT

An apparatus for monitoring an electrophysiological signal within a magnetically sensitive apparatus comprises a stretchable elastic cap having a plurality of electrode holders designed to be filled with a conductive electrolyte. Electrodes are disposed within the electrode holders and leads extend from the electrodes. The electrodes and the leads are made of a non-ferromagnetic conductive material.

25 Claims, 8 Drawing Sheets

FMRI COMPATIBLE ELECTRODE AND ELECTRODE PLACEMENT TECHNIQUES

CROSS REFERENCE TO RELATED APPLICATIONS

This application claims priority to provisional U.S. patent application Ser. No. 60/107,918, filed Nov. 10, 1998 by Don DuRousseau, the contents of which are incorporated herein by reference in their entirety.

FIELD OF THE INVENTION

The present invention relates to medical devices and more specifically to techniques for acquiring uncontaminated electrical signals from the brain and body, without the use of pre-amplification electronics, especially while located within the harsh operating environment produced by a functional magnetic resonance imaging (fMRI) system.

BACKGROUND OF THE RELATED ART

Conventional EEG, EOG, ECG, EMG, and other physiological signals are typically recorded using individually placed electrodes that are fixed on the scalp and body with adhesives or by the use of a cap type system. Examples of these techniques are those developed by Sams et al (U.S. Pat. No. 4,085,739) or Gevins et al (U.S. Pat. Nos. 4,967,038 and 5,038,782). In these placement methods, the electrodes are attached to amplifiers used to acquire and record the related electrical and physiological activity. These amplifier systems require a very low impedance contact with the skin and are very susceptible to emissions from other electrical equipment, such as an MRI device. In such an environment, the input stage of a conventional EEG, ECG or EMG amplifier is susceptible to the very large induced electrical and magnetic fields generated by a magnetic resonance imager to the point where the amplifier cannot function properly. In addition, these amplifier systems are almost always powered from an AC Voltage source and, therefore, radiate electromagnetic interference (EMI), which causes contamination of the anatomical and functional data acquired by the fMRI system and compromises the integrity of these data.

A prior attempt to collect EEG signals within the fMRI environment, by Ives et al (U.S. Pat. No. 5,445,162) is based on a battery powered analog pre-amplifier system in which individual electrodes are glued to the scalp and the electrical activity is amplified within the bore of the imaging device. The signals are then converted to light energy by additional analog circuits placed nearby the patient. While still within the harsh fMRI environment, these signals are communicated along fiber-optic cables outside the shielded room, which protects the imaging equipment from unwanted interference, to a secondary amplifier system that is located outside the shielded room and attached to a PC for collecting and processing the data. However, this optically coupled pre-amplification system is expensive, bulky, and cumbersome to operate. In addition, due to size restrictions within the head coil (located inside the imager) and the inability to use digital circuits in the design, due to broadcast interference from internal clock circuits, the AC-coupled nature of this devices makes it susceptible to large artifacts caused by transient signals produced during normal operation of the imaging system.

SUMMARY OF THE INVENTION

The problems of the prior art, described above, are solved, in accordance with the present invention, by providing an EEG Electrode Positioning System using an elastic head cap (hereinafter Quik-Cap), to position electrodes on the head and face to acquire electrical signals and communicate them to external amplifier equipment. The Quik-Cap provides a stretchable elastic cap and chinstrap portion capable of comfortably fitting a wide range of head size and shape variability. The Quik-Cap provides a plurality of electrode holders designed to be filled with a conductive electrolyte. In addition, the Quik-Cap provides a wire harness assembly that can be configured with either carbon or metal lead wires and is capable of interfacing with any type of commercially available amplifier system.

Some specific features and objectives of the invention include the following.

The present invention provides a low cost system for rapidly applying large numbers of electrodes on the head and body that is capable of acquiring signals inside an fMRI system and communicating them outside the shielded environment without the use of any electronic amplification.

It is another objective of the present invention to use carbon lead wires attached to the electrodes positioned on the head and body to limit the susceptibility of the system to contamination from an MRI system and to communicate signals outside a shielded fMRI environment to amplifiers attached to a PC for collecting and processing electrophysiological and other physiologically correlated data.

Another object of the present invention to use metal electrodes composed of Tin, Gold, Silver-Chlorided Silver, or a combination or amalgam of Silver-Chloride powders, each carried in soft rubber electrode mounts and connected to carbon lead wires to limit the susceptibility of the system to physiological and electronically induced contamination.

It is a still further object of the present invention to use carbon, carbonized plastic, or conductive plastic electrodes in connection with carbon lead wires to further limit the susceptibility of the system to physiological and electronically induced contamination.

It is a still further object of the present invention to use needle electrodes, implantible depth electrodes, or cortical surface electrodes in connection with carbon lead wires to further limit the susceptibility of the system to physiological and electronically induced contamination while recording signals directly from the brain or spinal chord.

It is a still further object of the present invention that a single electrode, or group of electrodes, may also be used to acquire signals from the eyes, heart or muscles, by providing a mechanism to position electrodes in the appropriate regions of the scalp, face, chest or body.

Still another object of the present invention is to permit a single lead wire, or group of lead wires, to be used to connect to and communicate signals from external transducer devices used to measure signals related to oxygen uptake, respiration, heart rate, impedance, motion, acceleration, force or other such signals.

Yet another feature of the present invention is to provide separable elastic cap, chinstrap, and wire harness portions to position electrode holders and electrodes on the head, face and body to acquire EEG, EOG, EMG, ECG and other physiologically correlated signals from humans while inside a magnetic resonance imaging system.

The foregoing and other features, aspects and advantages of the present invention will become more apparent from the following detailed description of the present invention when taken in conjunction with the accompanying drawings.

BRIEF DESCRIPTION OF THE DRAWINGS

The objects, features and advantages of the system of the present invention will be apparent from the following description in which.

DETAILED DESCRIPTION OF THE PREFERRED EMBODIMENTS

Figure 1:
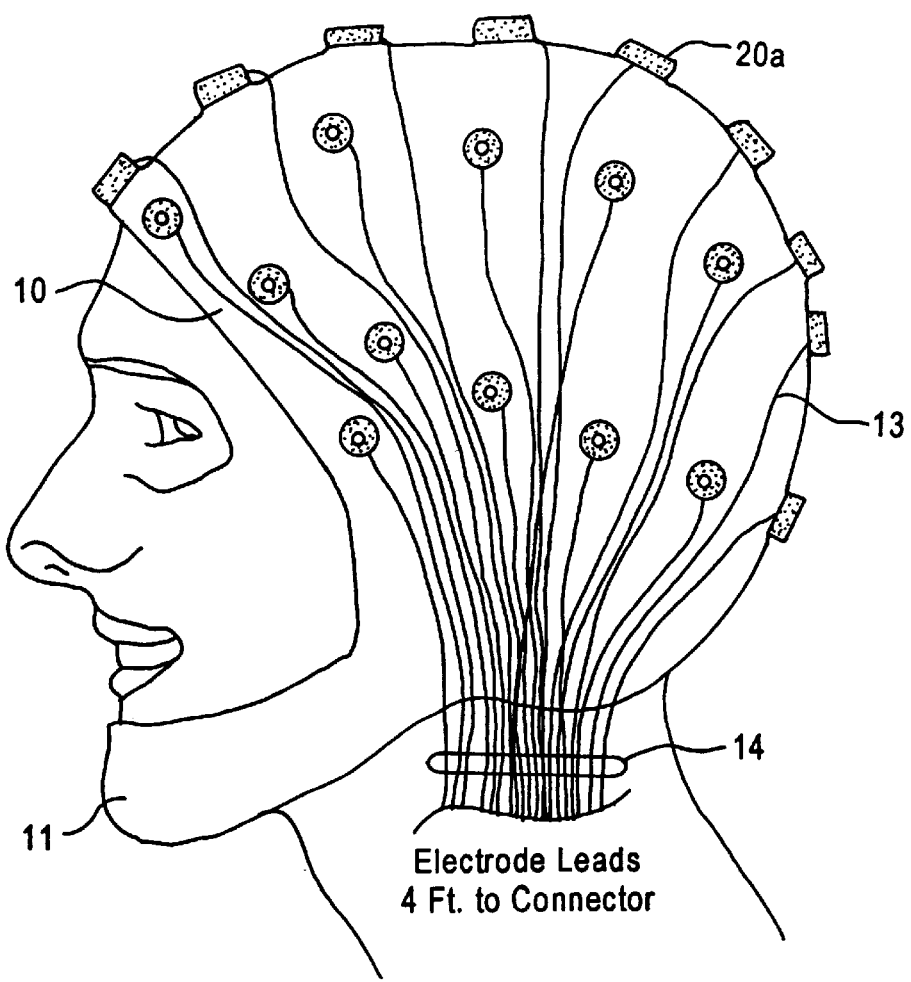
FIG. 1 is a side view of the elastic cap and chinstrap portion of an exemplary embodiment of the present invention showing electrode holders and lead wire harness assembly in which individual lead wires are attached to electrodes (not shown) carried within the electrode holders.
Figure 2A:
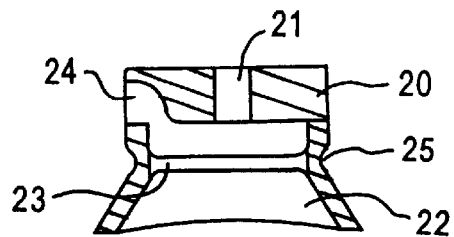
FIG. 2A is a cross-sectional side view of the electrode holder of FIG. 1.
Figure 2B:
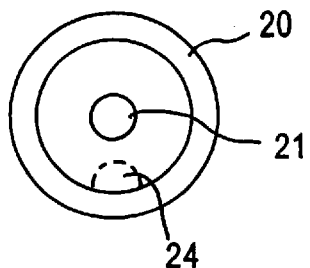
FIG. 2B is a top plan view of the embodiment of FIG. 2A.
Figure 2C:
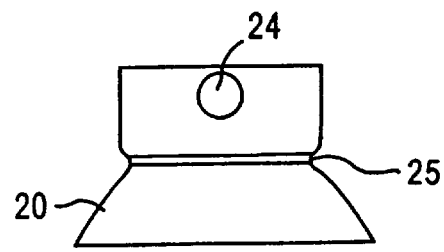
FIG. 2C is a side plan view of the embodiment of FIG. 2A.
Figure 2D:
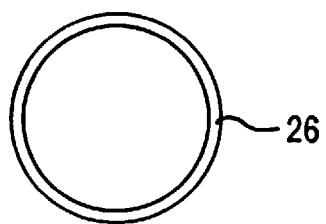
FIG. 2D is a top-down view of a rubber O-ring used to attach the electrode holder to the elastic cap portion of FIG. 1.

As shown in FIG. 1, the fMRI-compatible electrode placement system of the present invention includes an elastic fabric cap portion 10 and chinstrap portion 11, both composed preferably of a combined Lycra-Spandex™ material such as Style #: 96175 Black-09000, manufactured by Liberty Fabrics, 13441 Liberty Lane, Gordonsville, Va.).

Attached to the elastic cap portion 10, is a plurality of electrode holders 20a–n. The designation "n" means that the number depends on the number of electrodes desired. In typical usage, for example, n may be in the range from 1 to 1024. Also in FIG. 1, a plurality of lead wires 13 of the present invention form a harness assembly 14. The lead wires may be constructed of any non-ferromagnetic conductive material, but are preferably made of carbon. The lead wires may be wrapped in groups with flexible wrapping material (not shown), and extend from the electrodes (not shown) carried within the electrode holders 20a–n away from the head, terminating in a connector, such as a CHG-Series 40 pin connector (not shown) manufactured by 3M, Inc. The flexible wrapping (not shown) is used to ensure the wires will not be allowed to coil while inside the MRI environment in order to prevent induced heating of the lead wire material.

As shown in FIGS. 2A–2D, the electrode holder 20 is preferably constructed from a single piece of molded medical grade EPDM rubber, such as compound L-5099. The electrode holder 20, provides a central hole portion 21, which allows access to the central well portion 22, and which passes down to the scalp surface. Electrolyte is injected through the central hole 21 to fill the central well portion 22 creating a bridge to conduct the electrical signal from the skin surface to the electrode (not shown), which rests on the ridge portion 23 located within the central well portion 22 of the electrode holder 20. On the side of the electrode holder 20, near the top, a hole 24 exists where a lead wire attachment portion of the electrode (not shown) extends from the electrode holder. On the outside portion of the electrode holder 20, an indentation 25 exists in which two O-rings 26 are used to capture the elastic fabric of the cap 10 from above and below when the electrode holder is pushed through the elastic cap fabric 10.

Figure 3A:
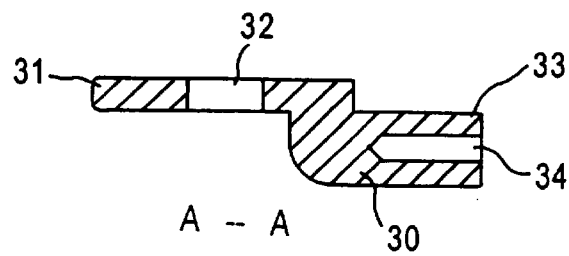
FIG. 3A is a cross-sectional side view along line A—A of FIG. 3B of an exemplary electrode carried within the electrode holder of FIG. 2A.
Figure 3B:
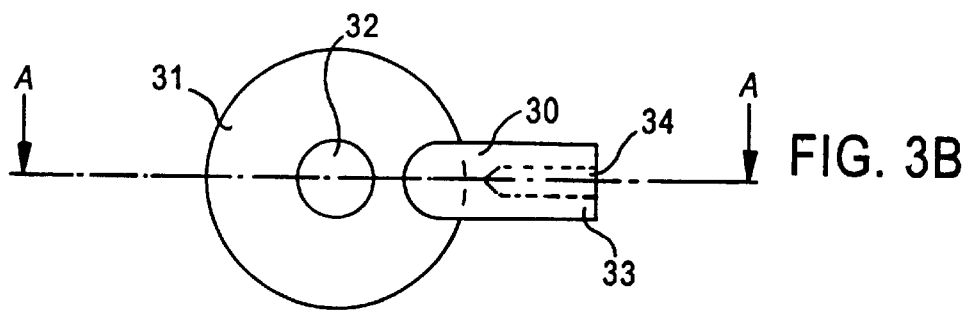
FIG. 3B is a top plan view of the embodiment of FIG. 3A.
Figure 3C:
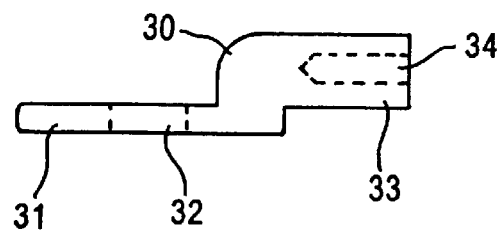
FIG. 3C is a side plan view of the embodiment of FIG. 3A.
Figure 4A:
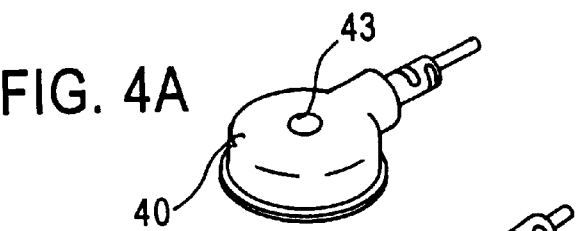
FIG. 4A is a perspective top view of an alternative embodiment of a cup shaped electrode carried in an exemplary electrode holder of FIG. 2A.
Figure 4B:
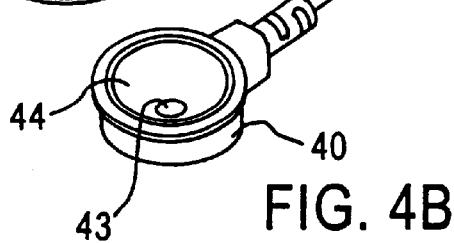
FIG. 4B is a perspective bottom view of an alternative embodiment using a cup shaped electrode carried in the electrode holder of FIG. 2A.
Figure 4C:
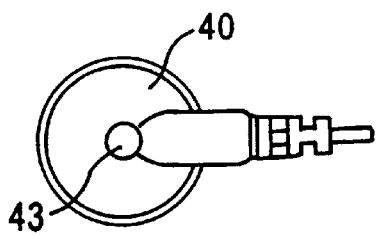
FIG. 4C is a top-down view of the embodiment of the electrode of FIG. 4A.
Figure 4D:
FIG. 4D is a side view of the embodiment of the electrode of FIG. 4A.
Figure 4E:
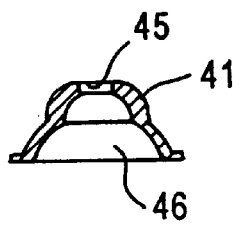
FIG. 4E is a cross-sectional view of an alternative embodiment of a conductive plastic electrode embodiment carried in the electrode holder of FIG. 2A.
Figure 4F:
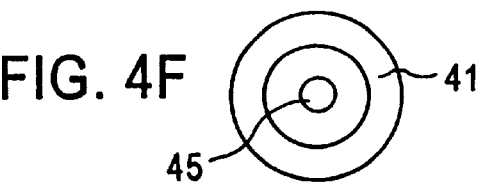
FIG. 4F is a top plan view of the embodiment of the electrode in FIG. 4E.
Figure 5A:
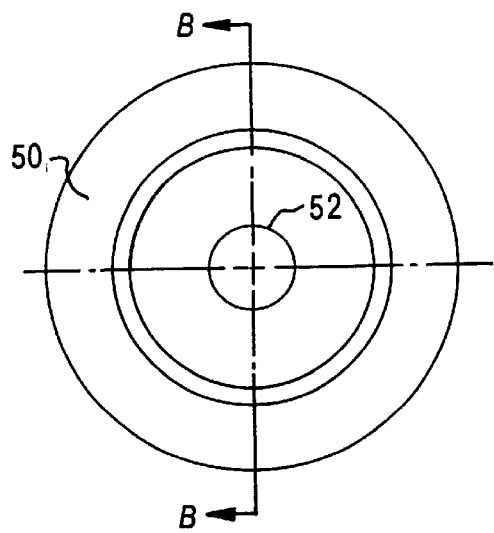
FIG. 5A is a top plan view of an alternative embodiment of a conductive plastic electrode embodiment carried in the electrode holder of FIG. 2A.
Figure 5B:
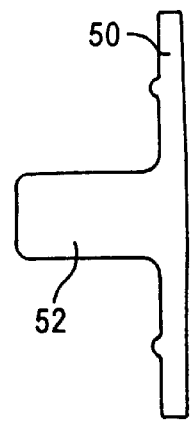
FIG. 5B is a cross-sectional side view along line B—B of the embodiment of the conductive plastic electrode of FIG. 5A.
Figure 5C:
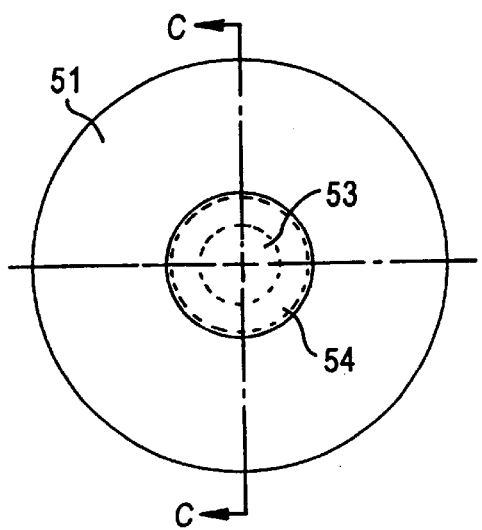
FIG. 5C is a top plan view of an alternative embodiment of a carbon electrode embodiment carried in the electrode holder of FIG. 2A.
Figure 5D:
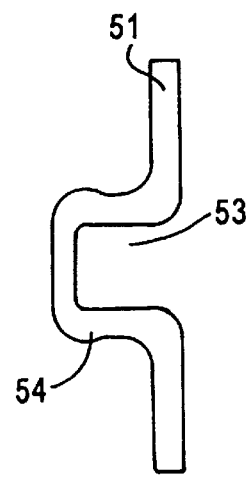
FIG. 5D is a cross-sectional side view along line C—C of the embodiment of the carbon electrode of FIG. 5C.

As shown in FIGS. 3A–3C, the electrode 30 of the present invention as a flat disk portion 31 with a central hole 32. The electrode 30 also includes a lead wire attachment portion 33, which extends outward from the flat disk portion 31 and provides a pathway 34. Such a pathway may be created by drilling or by other mechanisms. The drilled pathway 34 provides an opening in which the lead wire 13 passes and is attached to the electrode 30 by crimping the attachment portion 33 onto the lead wire 13.

In a typical assembly sequence, an O ring is slipped over the lead wire 13. The electrode 30 is inserted into the central well portion 22 of the electrode holder 20 and rests on the ridge portion 23 to ensure correct placement. The electrode holder is inserted through a button hole or other opening in the elastic fabric cap and secured by positioning one or more O-rings over the fabric. The lead wire 13 is placed into the pathway 34 and the attachment portion 33 is crimped onto the lead wire.

An alternative embodiment of the preferred electrode of the present invention is shown in FIGS. 4A–4F, where typical cup shaped electrodes 40 may be composed of metal (such as those manufactured by Specialized Laboratory Equipment, 232 Selsdon Rd. South Croydon Surrey, UK, PN: BO196/02) or conductive plastic 41 (such as those manufactured by Plastics One, 6591 Merriman Rd., S.W., Roanoke, Va., PN: 36562). In a typical metal electrode, a central hole 43 exists to allow injection of electrolyte down to the skin surface. In addition, a well portion 44 is provided to hold electrolyte in contact with the electrode surface. In a typical conductive plastic electrode 41, a central hole 45 exists to allow injection of electrolyte down to the skin surface. Again, a well portion 46 is provided to hold electrolyte in contact with the electrode surface. Both types of electrodes 40 and 41, may be readily carried within the electrode holder 20 of the present invention.

An alternative embodiment of the preferred electrode of the present invention is shown in FIGS. 5A–5D, where conductive plastic electrodes 50 (such as those manufactured by Select Engineering Inc., 260 Lunenburg St., Fitchburg, Mass., PN: SRT-3001/LP/0.06) and carbon electrodes 51 (such as those manufactured by Select Engineering Inc., 260 Lunenburg St., Fitchburg, Mass., PN: SRT-2001/CF/40) are shown. In both cases the non-metallic nature of the electrode material makes them less susceptible to induced currents present in the MRI environment, as well as to other physiological artifacts caused by movement of the body within the MRI device. On the conductive plastic electrode 50, a lead wire attachment means 52 exists, which provides a surface where conductive epoxy (such as EPO-TEK E2101) is used to attach the carbon lead wire 13 to the conductive plastic electrode 50. On the carbon electrode 51, a well portion 53 exists to hold electrolyte in contact with the electrode surface. The lead wire 13 is attached to the carbon electrode 51 by use of conductive epoxy at the electrode attachment point 54. Both the conductive plastic electrode 50 and carbon electrode 51 may be carried within electrode holder 20 of the present invention.

Figure 6:
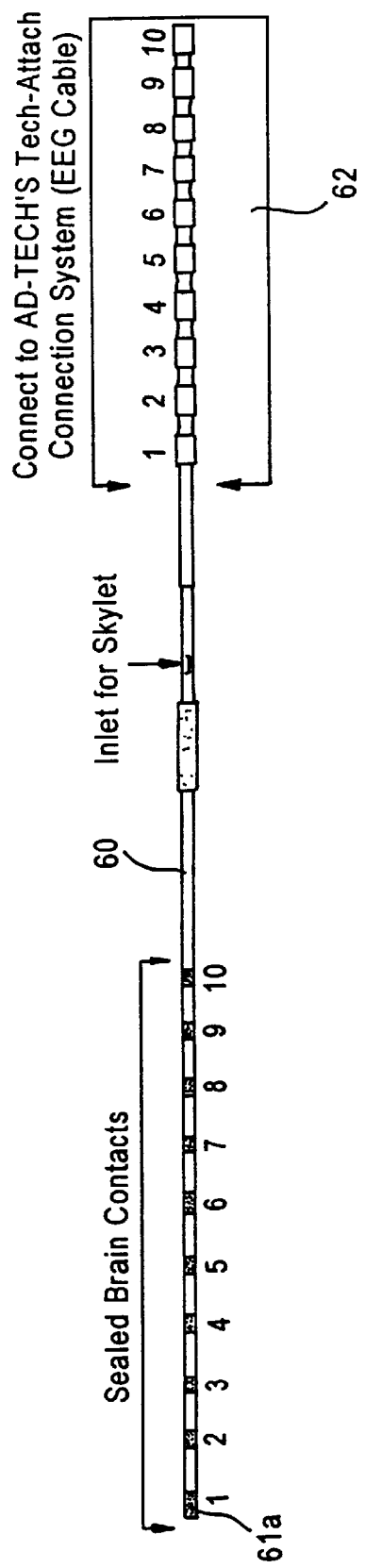
FIG. 6 is a top plan view of an alternative embodiment of a cortical depth electrode embodiment used with the carbon lead wire harness of the present invention.

An alternative embodiment of the preferred electrode of the present invention is shown in FIG. 6, where an implantible depth electrode assembly 60 (such as those manufactured by AD-Tech Medical Instrument Corp., 1901 William St., Racine, Wis., PN: SP-10P) is used. The depth electrode assembly 60 of the present embodiment positions 10 discreet electrodes 61*a–j* in which each acquires signals from a different region of the brain. The depth electrode assembly 60 can be placed into the cortex of a patient to collect electrical signals from multiple deep regions of the brain simultaneously. The depth electrode assembly 60 would not be carried in the electrode holder 20 of the present invention but rather the lead wire harness assembly 14 directly interfaces to the depth electrode assembly Connection System 62.

Figure 7:
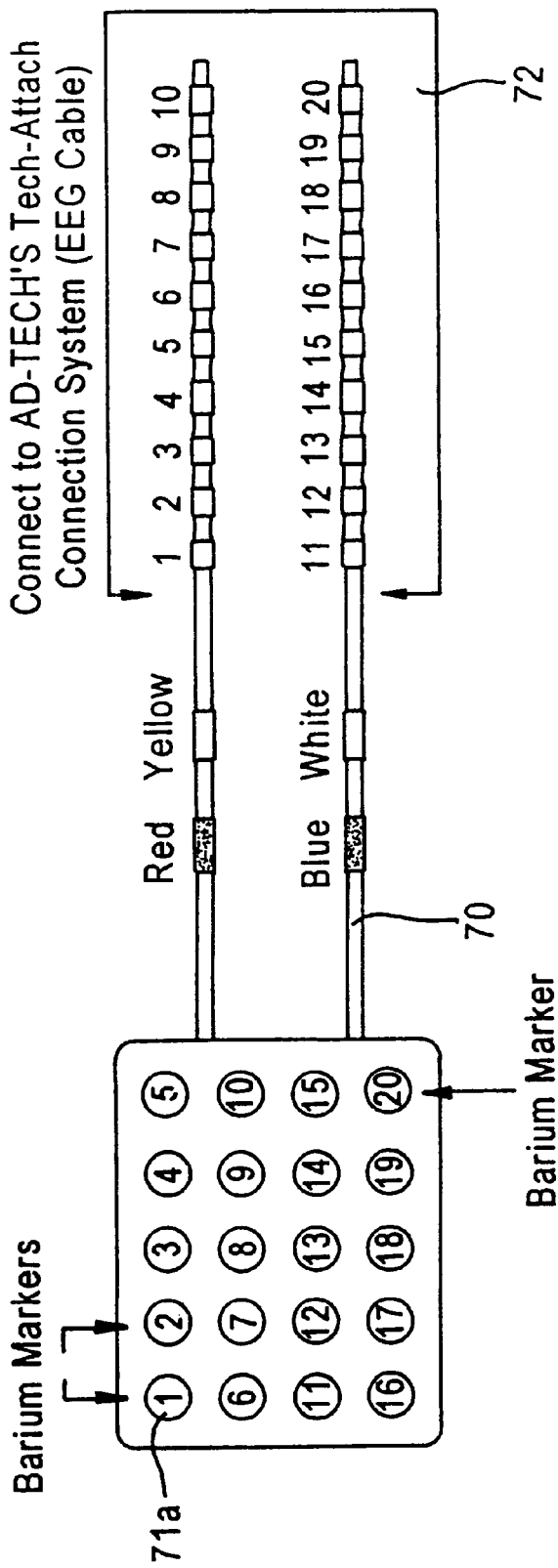
FIG. 7 is a top plan view of an alternative embodiment of a cortical surface grid electrode embodiment used with the carbon lead wire harness of the present invention.

An alternative embodiment of the preferred electrode of the present invention is shown in FIG. 7, where a subdural cortical surface electrode assembly 70 (such as those manufactured by AD-Tech Medical Instrument Corp., 1901 William St., Racine, Wis., PN: T-WS-20) is used. In the example given, the subdural cortical surface electrode assembly 70 of the present embodiment positions 20 discreet electrodes 71*a–t* in a grid pattern in which each acquires signals from a different region of the brain. However, other subdural cortical surface electrode assemblies exist that provide different numbers of electrodes. Grids with up to 128 discreet electrodes (not shown) are readily able commercially, but other numbers of electrodes may be used. The subdural cortical surface electrode assembly 70 can be placed on the cortex of a patient to collect electrical signals from multiple regions of the brain underlying the grid pattern formed by the electrodes of the assembly. The subdural cortical surface electrode assembly 70 would not be carried in the electrode holder 20 of the present but rather the lead wire harness assembly 14 would be directly connected to the subdural cortical surface electrode assembly Connection System 72.

Figure 8:
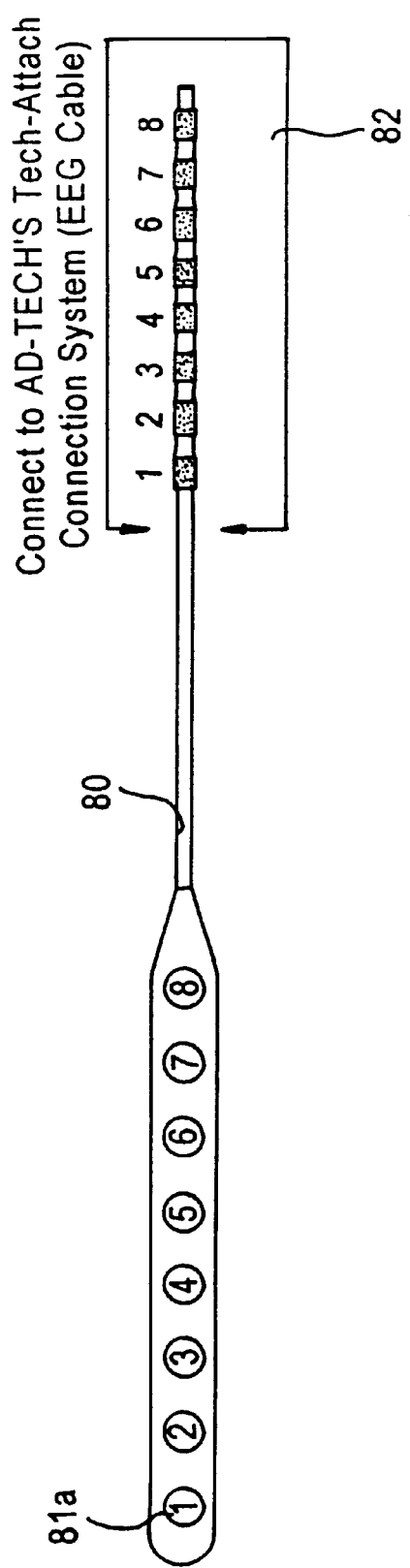
FIG. 8 is a top plan view of an alternative embodiment of a cortical surface strip electrode embodiment used with the carbon lead wire harness of the present invention.

An alternative embodiment of the preferred electrode of the present invention is shown in FIG. 8, where a subdural cortical surface electrode assembly 80 (such as that manufactured by AD-Tech Medical Instrument Corp., 1901 William St., Racine, Wis, PN: T-WS-8) is used. The subdural cortical surface assembly 80 of the present embodiment positions 8 discreet electrodes 81*a–h* in a strip pattern in which each acquires signals from a different region of the brain. However, other subdural cortical surface electrode assemblies are readily available commercially that provide from 1 up to 128 discreet electrodes (not shown). The subdural cortical surface electrode assembly 80 can be placed on the cortex of a patient to collect electrical signals from multiple regions of the brain underlying the strip pattern formed by the electrodes of the assembly. The subdural cortical surface electrode assembly 80 would not be carried in the electrode holder 20 of the present invention but would be directly connected to the lead wire harness assembly 14 through the assembly Connection System 82.

In operation, the assembled Quik-Cap is placed on the patient's head and then, in appropriate embodiments, each electrode holder is filled with conductive electrolyte. Slight abrasion of the skin may be required during placement to reduce the impedance at the skin electrolyte interface to acceptable levels as determined by the input characteristics of the amplifier system to which the Quik-Cap assembly is attached.

In the manner described, the problems associated with collection of patient data in the environment of an MRI can be overcome.

In this disclosure, there is shown and described only the preferred embodiments of the invention, but as mentioned above, one should understand that the invention is capable of use in various other combinations and environments and is capable of changes or modifications within the scope of the inventive concepts as expressed herein.

What is claimed is:

1. An apparatus for collecting physiological electrical signals inside of a magnetic resonance imaging system (MRI) during normal operation of the MRI system, the apparatus comprising:

a plurality of electrodes wherein the electrodes are made of a non-ferromagnetic conductive material;

one or more electrode leads connected to said electrodes wherein the leads are made of a nonferromagnetic conductive material and wherein at least two electrode leads are enclosed by flexible material configured to prevent coiling.

2. The apparatus of claim 1, wherein the electrodes are manufactured from a material selected from the group consisting of: Silver, Tin, Gold, Carbon, Platinum, Iridium, Silver/Silver Chloride, Conductive Plastic, Carbonized Plastic and Carbon Fibers.

3. The apparatus of claim 1, wherein the electrodes are subdermal needles, subdural cortical surface electrodes, or subdural depth electrodes.

4. The apparatus of claim 1, wherein the electrode leads are manufactured from a material selected from the group the group consisting of:

Silver, Tin, Gold, Carbon, Platinum, Iridium, Silver/Silver Chloride, Conductive Plastic, Carbonized Plastic and Carbon Fibers.

5. The apparatus of claim 1, wherein each of said one or more electrodes is positioned within an electrode holder.

6. The apparatus of claim 5, wherein the electrode holder is configured to accommodate one or more O-rings.

7. The apparatus of claim 5, wherein the electrode holder is made of a flexible material.

8. An apparatus for collecting physiological electrical signals inside of a shielded environment of a functional magnetic resonance imaging (MRI) system during normal operation of the MRI system and carrying such signals without amplification outside of the shielded environment, the apparatus comprising:

one or more electrodes, one or more non-amplifying electrode lead connected to aid electrodes, wherein at least two electrode leads are enclosed by flexible material configured to prevent coiling, and wherein the electrode leads are manufactured from a material selected from the group consisting of: Silver, Tin, Gold, Carbon, Platinum, Iridium, Silver/Silver Chloride, Conductive Plastic, Carbonized Plastic, and Carbon Fibers, whereby the apparatus is configured to not interfere with the integrity of MRI data.

9. An apparatus for collecting physiological electrical signals inside of a shielded environment of a functional magnetic resonance imaging (MRI) system during normal operation of the MRI system and carrying such signals without amplification outside of the shielded environment, the apparatus comprising:

one or more electrodes, and one or more non-amplifying electrode leads connected to said electrodes, wherein the electrode leads conduct signals over a distance of more than 10 feet, whereby the apparatus is configured to not interfere with the integrity of MRI data.

10. An apparatus for collecting physiological electrical signals inside of a shielded environment of a functional magnetic resonance imaging (MRI) system during, normal operation of the MRI system and carrying such signals without amplification outside of the shielded environment, the apparatus comprising:

one or more electrodes, one or more electrode holders having an electrode positioned therein, and wherein the electrode holder contains an opening through which electrolyte can be applied to the patient; and one or more non-amplifying electrode leads connected to said electrodes, wherein the leads conduct signals over a distance of more than 10 feet, whereby the apparatus is confined to not interfere with the integrity of MRI data.

11. An apparatus for collecting physiological electrical signals inside of a shielded environment of a functional magnetic resonance imaging (MRI) system during normal operation of the MRI system and carrying such signals without amplification outside of the shielded environment, the apparatus comprising;

one or more electrodes, one or more rubber electrode holders having an electrode positioned therein, and wherein the electrode holder contains an opening through which electrolyte can be applied to the patient, and one or more non-amplifying electrode leads connected to said electrodes, wherein the leads conduct signals over a distance of more than 10 feet, whereby the apparatus is configured to not interfere with the integrity of MRI data.

12. An apparatus for collecting physiological electrical signals inside of a shielded environment of a functional magnetic resonance imaging (MRI) system during normal operation of the MRI system and carrying such signals without amplification outside of the shielded environment, the apparatus comprising:

one or more electrodes, an elastic cap for placement on a patient's head;

a plurality of electrode holders mounted to the cap; and one or more non-amplifying electrode leads connected to said electrodes, wherein the leads conduct signals over a distance of more than 10 feet, whereby the apparatus is configured to not interfere with the integrity of MRI data.

13. An apparatus for collecting physiological electrical signals during normal operation of a Magnetoencephalography (MEG) system and carrying such signals without amplification outside of the shielded environment of the MEG system, the apparatus comprising:

a plurality of nonmetallic electrodes; and one or more electrode leads connected to said electrodes wherein the leads are made of a non-ferromagnetic conductive material and wherein at least two electrode leads are enclosed by flexible material configured to prevent coiling.

14. An apparatus for collecting physiological electrical signals inside of a shielded environment of a functional magnetic resonance imaging (MRI) system during normal operation of the MRI system or an operating magnetoencephalography (MEG) system and carrying such signals without amplification outside of the shielded environment, the apparatus comprising:

one or more electrodes being held in place by a flexible wrapping material; and one or more electrode leads connected to said electrodes wherein the leads are made of a non-ferromagnetic conductive material and wherein at least two electrode leads are enclosed by flexible material configured to prevent coiling.

15. A method of collecting electrical data inside of a shielded environment of a functional magnetic resonance imaging (MRI) system during normal operation of the MRI system without interfering with the integrity of the MRI data, the method comprising the steps of:

placing one or more electrodes in dermal contact with a patient located inside of the shielded environment;

connecting said electrodes to one end of a lead wire;

connecting a second end of said lead wire to an amplifier system located outside of said shielded environment.

16. The method of claim 15, wherein said electrodes are made from a non-ferromagnetic material.

17. The method of claim 15, wherein said lead wires are made from a non-ferromagnetic material.

18. The method of claim 16 or 17 wherein said non-ferromagnetic material is one of a the group consisting of: Silver, Tin, Gold, Carbon, Platinum, Iridium, Silver/Silver Chloride, Conductive Plastic, Carbonized Plastic and Carbon Fibers.

19. The method of claim 15, further comprising the steps of:

mounting one or more electrode holder in a flexible cap; and inserting said electrodes into said electrode holders.

20. The method of claim 19, further comprising, the step of wrapping said lead wires with a flexible material.

21. The method of claim 19, further comprising the step of securing said flexible cap to the head of said patient ting a strap.

22. The method of claim 21, further comprising the step of adjusting the length of the strap using at least one Velcro™ connection between the strap and the cap.

23. The method of claim 15, further comprising the step of mounting at least one of the electrodes to a patient using a flexible wrapping to prevent coiling.

24. An apparatus for collecting electrophysiological data in a magnetically sensitive environment, the apparatus comprising:

a signal amplification system;

an electrode made of a non-ferromagnetic material;

a lead made of a non-ferromagnetic material and extending from the electrode, the lead being conductively coupled to the signal amplification system and being of sufficient length to enable the signal amplification system to be placed beyond the magnetically sensitive environment.

25. A method of collecting electrophysiological data in a magnetically sensitive environment, the method comprising:

providing a plurality of electrodes wherein the electrodes are made of a non-ferromagnetic conductive material; and connecting said electrodes to leads made of a non-ferromagnetic conductive material; and enclosing the leads in a flexible material configured to prevent coiling.

* * * * *